Figure 1:
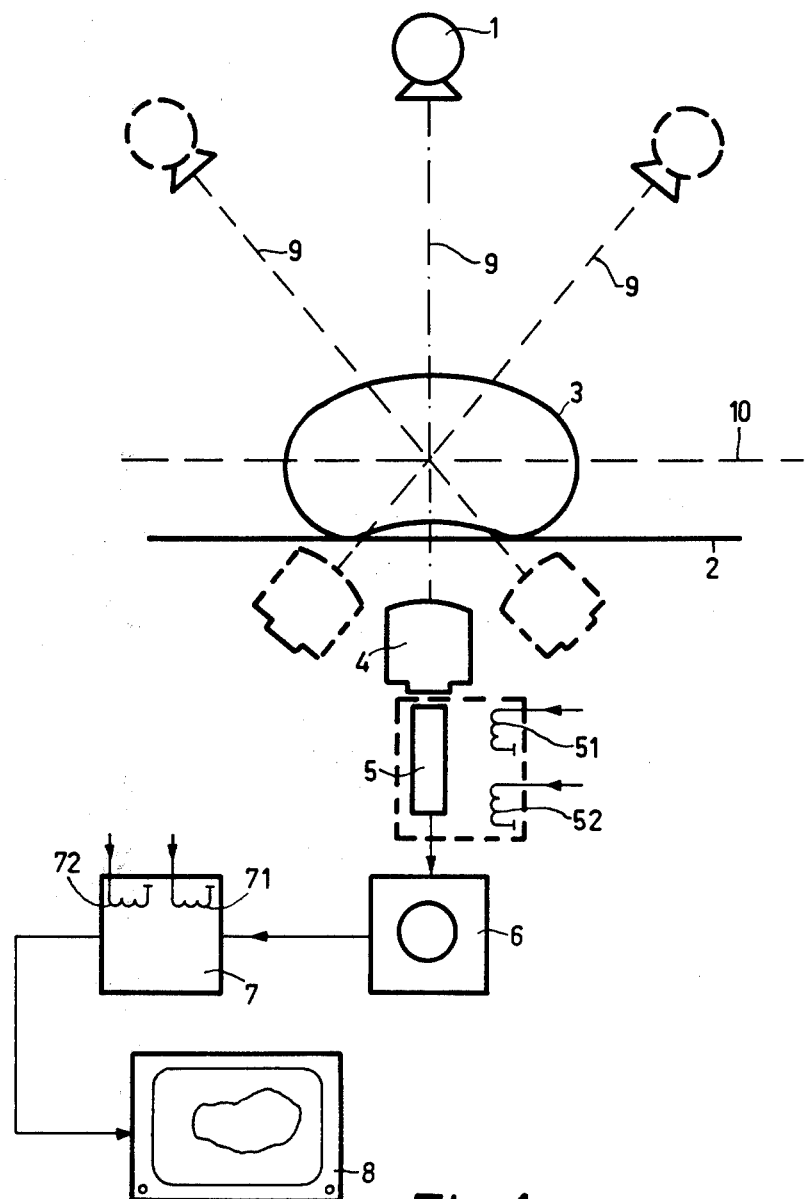

United States Patent [19]

Dittrich et al.

[11] 4,207,595
[45] Jun. 10, 1980

[54] APPARATUS FOR MAKING LAMINAR RADIOGRAMS

[75] Inventors: Jürgen Dittrich, Marschacht; Jürgen Heinzerling; Peter Lux, both of Hamburg, all of Fed. Rep. of Germany

[73] Assignee: U.S. Philips Corporation, New York, N.Y.

[21] Appl. No.: 862,688

[22] Filed: Dec. 21, 1977

[30] Foreign Application Priority Data

Apr. 28, 1977 [DE] Fed. Rep. of Germany ....... 2718943

[51] Int. Cl.² .................. H04N 5/32; G03B 41/16; G01M 23/00
[52] U.S. Cl. .................. 358/111; 250/416 TV; 250/445 T
[58] Field of Search .................. 358/111; 250/445 T, 250/362, 363 S, 416 TV

[56] References Cited

U.S. PATENT DOCUMENTS

| | | | |
|---|---|---|---|
| 3,622,786 | 11/1971 | Walker et al. | 358/111 X |
| 3,852,602 | 12/1974 | Gramm et al. | 250/363 S X |
| 3,973,128 | 8/1976 | LeMay | 250/320 X |
| 3,976,885 | 8/1976 | Brunnett et al. | 250/363 S X |
| 3,983,399 | 9/1976 | Cox, Jr. et al. | 250/363 S X |
| 4,008,400 | 2/1977 | Brunnett et al. | 250/455 T |
| 4,053,780 | 10/1977 | Sparks | 250/455 T |
| 4,066,903 | 1/1978 | LeMay | 250/455 T X |
| 4,071,760 | 1/1978 | LeMay | 250/363 S |
| 4,075,492 | 2/1978 | Boyd et al. | 250/445 T |

OTHER PUBLICATIONS

1973 British Journal of Radiology, 46, 262–271; No. 544 (Apr. 1973), pp. 262–271, "A Radiosotope Scanner for Rectilinear, Arc, Transverse Sectio and Long Section Scanning".
1973 British Journal of Radiology, 46, 1016–1022; No. 552 (Dec. 1973), "Computerized Transverse Axial Scanning (Tomography) Part I".

Primary Examiner—John C. Martin
Assistant Examiner—Aristotelis M. Psitos
Attorney, Agent, or Firm—Thomas A. Briody; Jack Oisher; Jack E. Haken

[57] ABSTRACT

In tomosynthesis distortions are produced owing to the curvature of the image intensifier input screen and other non-linearities of the transmission system, which in particular affect the synthesis of the laminar image when the individual images should be shifted relative to each other for this purpose. These distortions depend on the angle which the central ray makes with the laminar plane during the individual exposures and therefore they can hardly be compensated for. The invention now proposes that when the individual images are taken the image intensifier is steered so that the optical axis always remains parallel to the central ray. The distortions produced by the curvature of the input screen of the image intensifier etc. are then independent of the angle between the central ray and the laminar plane, and can be compensated for by known commercially available correction devices. However, additional geometric distortion is then produced because the plane of the input screen is inclined relative to the laminar plane. These geometric distortions depend on the orbit angle. By a rotation of the deflection field in accordance with the orbit angle, it is then achieved that trapezium distortions are produced which are independent of the orbit angle. These trapezium distortions are compensated for in known manner, and subsequently the position of the deflection field is restored.

7 Claims, 6 Drawing Figures

APPARATUS FOR MAKING LAMINAR RADIOGRAMS

The invention relates to apparatus for making laminar radiograms with an image recording device, which comprises an image intensifier and a television camera for recording individual images in different positions of the X-ray radiator and of the image recording device, and with a superposition device for the formation of a laminar radiogram by the superposition of the individual images, preferably by means of an image storage tube, which images have been shifted relative to each other by predetermined amounts, the image recording device being arranged and steered so that its optical axis always extends parallel to the central ray, and there being provided a correction device which reduces distortions resulting from the construction of the image recording device, in accordance with the main patent . . . (Patent Application No. P 26 58 33.3).

It is an object of the above application to reduce distortions which may arise during the synthesis of a laminar radiogram from the individual images, if the individual images are shifted relative to each other and if the input screen of the image intensifier is curved. These distortions do not only depend on the curvature of the image-intensifier input screen, but also on the geometrical relations during recording, and therefore they can only be compensated for with great difficulty. Therefore, in accordance with the above application, the image recording device is steered so that its optical axis remains parallel to the central ray (which can for example be achieved in a simple manner in that the image recording device is suitably secured to the guide rod, which provides the mechanical coupling between the X-ray tube and the image recording device), so that the laminar plane and the plane of the input screen of the image intensifier make an angle with each other which is equal to the laminar angle (which is the angle between the central ray and the normal to the laminar plane). The above application is based on the recognition that with such a steering distortions as a result of the construction of the image recording device (distortions as a result of the electron optical system, as a result of the coupling objective between the output screen of the image intensifier and the television camera, and pin-cushion distortion owing to the curvature of the image intensifier input screen etc.) become independent of the geometrical relations during recording. Thus, these distortions can be compensated for by a known commercially available correction device.

However, because the image recording device is always steered so as to be parallel to the central ray, geometric distortions are produced because the laminar plane and the plane of the input screen of the image intensifier are no longer parallel to each other, but make an angle with each other which is equal to the laminar angle. For example, a rectangle in the laminar plane, whose sides respectively extend parallel and perpendicularly to the projection of the central ray on the laminar plane, is therefore imaged as a trapezium on the image intensifier input screen. The above application describes a circuit arrangement which eliminates these geometric distortions in that it for example deforms the deflection field of the television camera in the same way as the rectangle in the laminar plane is deformed on the input screen of the image intensifier, which screen is inclined relative to the laminar plane. As the geometric distortions depend on the orbit angle (which is the angle which the projection of the central ray on the laminar plane makes with a straight line-which is preferably perpendicular or parallel to the line scanning direction-), the correction to be performed differs for substantially each orbit angle, i.e. for each individual image.

It is the object of the present invention to provide a further device for eliminating these geometric distortions.

In accordance with the invention this object is achieved by (a) a circuit arrangement associated with the television camera or the image storage tube for electronically rotating the image field through the same angle through which the system X-ray radiator/image recording device is rotated when the individual images are recorded, in which components of vertical frequency are superimposed on the horizontal deflection and components of horizontal frequency are superimposed on the vertical deflection, (b) a circuit arrangement for trapezium correction, which follows the circuit arrangement for rotating the image field, and (c) means for restoring the position of the image field.

The invention is based on the recognition that owing to the rotation of the image field the geometric distortions which are produced are independent of the orbit angle of the laminar radiography apparatus when the individual image is recorded and only depends on the constructional geometry and on the laminar angle, which is usually the same for all individual images and is adjusted before operation. A rectangle in the laminar plane, whose sides extend parallel and perpendicular to the sides of a correspondingly rotated image field, will always appear on the input screen of the image intensifier as a trapezium and therefore, in order to eliminate the geometric distortions, only a trapezium correction is to be applied for which the scanning field of the television camera is to be subjected to the same trapezium distortion as the projection of the rectangle in the laminar plane on the plane of the input screen. Trapezium correction is also possible in the image storage tube during write-in of the individual image, but then the deflection field is to be deformed inversely, i.e. areas which are expanded by the projection should be contracted and vice versa. Restoring the position of the image field is necessary in order to enable a laminar radiogram to be obtained by superposition of the individual images.

As is known the coordinates x, y of a point in a stationary (x·y) coordinate system will change into the coordinates u, v in a rotating (u, v) coordinate system in accordance with the equations.

$$u = x \cdot \cos \phi + y \cdot \sin \phi \quad (1)$$

and $$v = y \cdot \cos \phi - x \cdot \sin \phi \quad (2)$$

where $\phi$ is the angle between for example the x-axis and the u-axis. The image field may also be rotated in accordance with the same equations. In that case x is a deflection current or a deflection voltage of horizontal or line frequency and y a deflection voltage or a deflection current of vertical or field frequency; $\phi$ is the orbit angle. The components u and v obtained by superposition are applied to the horizontal and the vertical deflection system respectively. As is evident from equation (1), the deflection signal u for the horizontal deflection in addition contains a vertical frequency component (y·sin $\phi$). Similarly, the deflection signal v for the vertical deflection contains a component of horizontal frequency (x·sin $\phi$).

It can be demonstrated that a point with the coordinates u and v in the laminar plane changes into a point u' and v' as a result of the trapezium distortions, the following relationship being valid $$u' = \frac{u \cdot \cos\alpha}{(1 + u \cdot c \cdot \sin\alpha)} \quad (3)$$

and $$v' = \frac{v}{(1 + u \cdot c \cdot \sin\alpha)} \quad (4)$$

Herein c is the reciprocal of the distance of the focus of the X-radiator from the image intensifier input plane. As this distance is great in comparison with the radius of the image intensifier input screen, the term u·c·sin $\alpha < 1$.

In order to eliminate this distortion it is merely necessary to deform the deflection field in the television camera in the same manner, i.e. instead of the deflection currents or deflection voltages u and v the deflection voltages or deflection currents u' and v' in accordance with equations (3) and (4) should be applied to the deflection units of the television camera. Devices by means of which such a trapezium correction can be obtained are well-known.

Instead of correction by the deformation of the deflection field of the television camera, it is also possible to deform the deflection field of the image storage tube when individual images are written in for the purpose of forming a laminar radiogram. However, in this case the deflection field is to be deformed inversely, i.e. areas which contract during projection on the image intensifier input screen should be expanded and vice versa. The equations for this are $$u' = \frac{u}{(\cos\alpha \cdot (1 - u \cdot c \cdot \tan\alpha)} \quad (5)$$

and $$v' = \frac{v}{(1 - u \cdot c \cdot \tan\alpha)} \quad (6)$$

If the image field of the television camera has been rotated, the position of the image field can be restored in that the image field of the image storage tube is rotated in exactly the same manner when the individual images are written in. However, it is also possible to restore the position of the image field of the television camera in accordance with the equations $$x'' = u'' \cos\phi - v'' \sin\phi \quad (7)$$

and $$y'' = u'' \sin\phi + v'' \cos\phi \quad (8)$$

When the image field is rotated by influencing the deflection of the image storage tube accordingly, restoring the position is also effected in accordance with equations (7) and (8).

Figure 2:
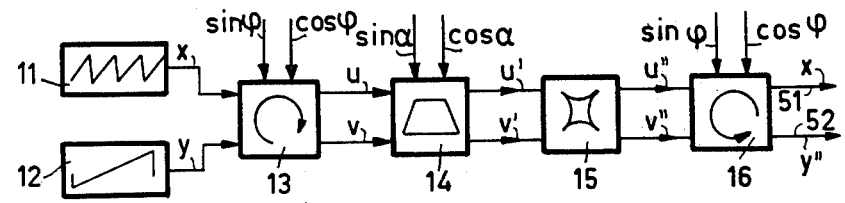
Figure 3:
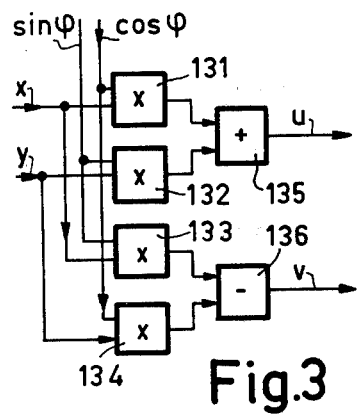
Figure 5:
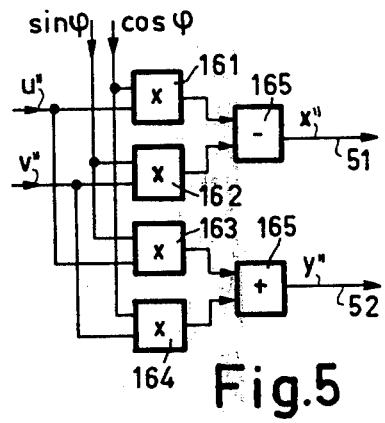
Figure 4:
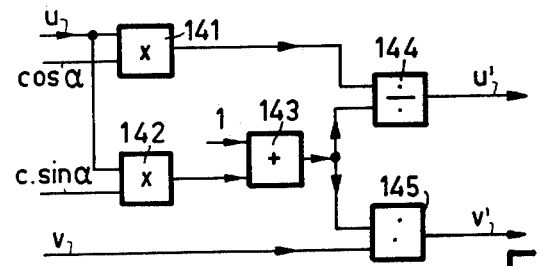
Figure 6:
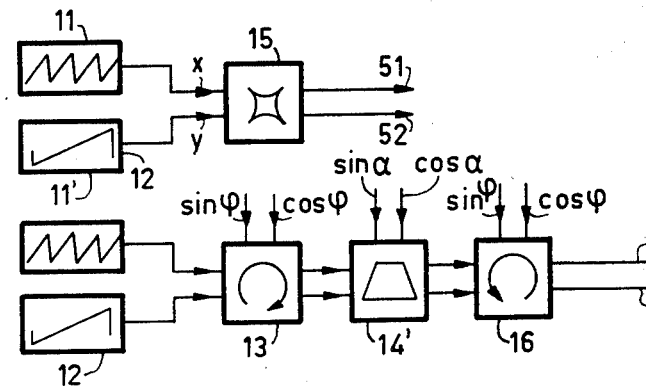

The invention will now be described in more detail with reference to the drawing which shows an embodiment. In the drawing FIG. 1 schematically shows an apparatus in accordance with the invention, the units which eliminate the distortions by deformation of the deflection field of the image storage tube and/or the television camera not being shown, FIG. 2 shows the block diagram of a circuit which eliminates the distortions by rotation and deformation of the deflection field of the television camera, FIG. 3 shows an example of the circuit section for rotation of the image field, FIG. 4 shows an example of the circuit arrangement for trapezium correction, FIG. 5 shows an example of the circuit for restoring the position of the image field, and FIG. 6 shows an embodiment in which on the camera side only the pin-cushion correction is performed which is necessitated by the curvature of the image intensifier input screen, whilst the geometric distortions which are produced are eliminated at the image storage tube.

In FIG. 1 an X-ray radiator is designated 1, whose radiation passes through the body of a patient 3 which is positioned on a table top 2. The ray transmission behind the patient is intercepted by an image intensifier 4 and converted into a visible image, which is recorded by a television camera 5, which comprises deflection coils 51 and 52 for the horizontal and vertical deflection respectively. The video signals then produced, which each correspond to an individual image, are transferred to a buffer memory 6, for example a disc memory, from which they can be extracted and stored in an image storage tube 7, which is equipped with deflection coils 71 and 72 for horizontal and vertical deflection respectively, for the formation of a superposition image. The relative shift of the individual images, which depends on the position of the laminar plane to be reproduced by superposition, is then computed by a control computer, not shown, which also controls the deflection units of the image storage tube 7 accordingly. The laminar radiogram obtained by superposition can be read from the target of the image storage tube 7 and displayed by a display unit 8. So far the construction of the apparatus shown in FIG. 1 is known.

The individual images are taken in different positions of the system radiator/image recording device (image intensifier 4 and television camera 5), which are generally situated on a circle which is parallel to the laminar plane. FIG. 1 shows three of these positions, two positions being represented by dashed lines only. The point of intersection of the central rays 9 determines the position of the plane 10, which can be reproduced sharply by superposition of the individual images without relative shifting.

In FIG. 1 it can be seen that the image recording device including the image intensifier 4 and television camera 5 is steered so that its optical axis (which is the line which is perpendicular to the centre of the image-intensifier input screen) always extends parallel to the central ray 9, whilst in known apparatus the image recording device is arranged so that in various positions its optical axis is perpendicular to the laminar plane 10. Steering the image recording device in such a way that its optical axis extends parallel to the central ray is simple, because most tomography equipment comprises a coupling rod which links the X-ray radiator and the image recording device to each other and causes them to be moved in opposite directions. This coupling rod extends parallel to the central ray and therefore it need only be linked to the image recording device in such a way that it extends parallel to the optical axis of the image recording device.

In this apparatus pin-cushion distortions are produced owing to the curvature of the image intensifier input screen, and other distortions for example owing to the electron-optical system and the objective between the image intensifier output screen and the input of the television camera, which distortions are independent of the geometry during recording, as well as distortions which depend on the geometry during recording. These distortions can be compensated for independently of each other.

FIG. 2 shows a circuit arrangement for the elimination of the distortions on the camera side. This circuit comprises two sawtooth generators 11 and 12 for generating a sawtooth-shaped output signal x and y, respectively with the horizontal and vertical deflection frequency respectively. The output signals x and y are applied to the inputs of a circuit 13 for electronically rotating the image field. This circuit modifies the input signals x and y into output signals u and v in accordance with equations (1) and (2). As a result of this, the field which is scanned on the target of the television camera is rotated through the angle $\phi$.

FIG. 3 shows an example of such a circuit arrangement. It comprises four multiplifer stages 131 ... 134, as well as an adder circuit 135 and a subtractor circuit 136. The one input of the multiplier circuits 131 and 133 is connected to the output of the sawtooth generator 11. As a result, it carries the sawtooth signal x of horizontal frequency. The corresponding input of the multiplier circuits 132 and 134 is connected to the output of the sawtooth generator 12 and consequently carries the sawtooth signal y of vertical frequency. The respective second inputs of the multiplier circuits 131 and 134 receive a signal which is proportional to the cosine of the orbit angle $\phi$, whilst the corresponding input of the multiplier circuits 132 and 133 receives a signal which is proportional to the sine of the orbit angle $\phi$. The outputs of the multiplier circuits 131 and 132 are connected to the two inputs of an adder circuit 135. The output signal u of this adder circuit consequently corresponds to equation (1). The outputs of the multiplier circuits 133 and 134 are connected to the two inputs of the subtractor circuit 136, which subtracts the output signal of the multiplier circuit 134 from the output signal of the multiplier circuit 133. It is evident that the output signal v satisfies equation (2).

The output signals u and v of the circuit for electronically rotating the image field are applied to a circuit 14 for trapezium correction. In this circuit the rotated rectangular deflection field is deformed in accordance with a trapezium, namely in the same way as a rectangle in the laminar plane is deformed during projection on the input screen of the image intensifier. FIG. 4 shows a circuit arrangement which is suitable for this purpose.

The circuit arrangement comprises a first multiplier circuit 141, in which the product u·cos $\alpha$ is formed, and a second multiplier circuit 142, of which one input receives the signal u, and of which the other input receives a signal which is proportional to the expression c·sin $\alpha$. The output signal of the multiplier circuit 142 is added to a signal corresponding to the number 1 in an adder circuit 143. The circuit furthermore comprises a first divider circuit 144, in which the output signal of the multiplier circuit 141 is divided by the output signal of the adder circuit 143, and a second divider circuit 145, in which the output signal v of the circuit arrangement 13 is divided by the output signal of the adder stage 143. It is evident that the output voltages u' and v' of the divider circuits 144 and 145 satisfy equations (3) and (4).

Since, as previously stated, the relationship:

$$u \cdot c \sin \alpha \ll 1$$

is valid, a very good approximation of equations (3) and (4) is obtained when the output signal of the multiplier circuit 141 and the signal v are multiplied by the factor $1 - u \cdot c \cdot \sin \alpha$. In this case the adder circuit 143 need only be replaced by a subtractor circuit, which subtracts the output signal of the multiplier circuit from the signal value 1, whilst the divider circuits 144 and 145 are each replaced by a multiplier circuit.

The output signals u' and v' of the circuit arrangement 14 are applied to the inputs of a correction device 15, which compensates for pin-cushion distortions owing to the curvature of the image intensifier input screen and, as the case may be, any further distortions caused by the electron optical system etc. Such correction devices are commercially available (for example, "Intronix Pincushion Distortion Module" from Infraton, Munich). The sequence of the circuits 14 and 15 for trapezium and pin-cushion correction respectively may also be reversed.

The output signal of the correction device 15 is applied to a circuit arrangement 16 for restoring the position of the image field, which circuit rotates the image field by the same amount as the circuit arrangement 13, but in an opposite sense. An example of this circuit arrangement is shown in FIG. 5.

The circuit arrangement comprises four multiplier stages 161 ... 164. The output signal u'' is multiplied by a signal which is proportional to the cosine of the orbit angle $\phi$ in the multiplier stage 161 and by a signal which is proportional to the sige of the orbit angle in the multiplier stage 163. Accordingly, the output signal v'' of the correction device 15 is multiplied by a signal which is proportional to the sine of the orbit angle $\phi$ in the multiplier stage 162 and the signal which is proportional to the cosine in the multiplier stage 164. The outputs of the multiplier stages 161 and 162 are connected to the inputs of a subtractor stage 165, which subtracts the output signal of the multiplier stage 162 from the output signal of the multiplier stage 161. The output signal x'' of the subtractor circuit consequently satisfies the equation (7). An adder circuit 165 adds the output signals of the multiplier stages 163 and 164. Its output signal y'' consequently satisfies equation (8). The output signals x'', y'' of the circuit arrangement 16 for restoring the position of the image field are applied to the deflection coils 51 and 52 of the television camera, as the case may be, via a suitable linear amplifier.

In the circuit arrangement shown in block schematic form in FIG. 6 pin cushion correction is effected on the camera side and the trapezium correction on the side of the image storage tube. The deflection signals from the sawtooth generators 11 and 12 are applied to the deflection coils 51 and 52 via the circuit 15, which compensates for pin-cushion distortions and other distortions caused by the electron-optical system etc. The deflection signals of the sawtooth generators 11' and 12' of the image storage tube 7 are applied to the deflection coils 71 and 72 of the image storage tube via a circuit 13 for rotation of the image field, a circuit 14' for trapezium correction, and a circuit 16 for restoring the position of the image field. The circuits 13 and 14 may be of the same design as the corresponding circuits in FIG. 2, FIG. 3 and FIG. 5 respectively. The trapezium correction circuit 14' should ensure that the deflection field is expanded when the projection on the image intensifier input screen is contracted and vice versa. The corresponding modifications in accordance with equations (5) and (6) can be realized in a simple way as in the example in accordance with FIG. 4.

What is claimed is:

1. In an apparatus for producing laminar radiograms including an X-ray radiator and an image recording device mounted to image a subject at different positions with the optical axis of the image recording device maintained parallel to the central ray of the X-ray radiator, the image recording device including an image intensifier and a television camera, the apparatus further including a superposition device for forming laminar radiogram corresponding to a laminar plane of the subject by superposing individual images shifted by different amounts with respect to one another, and wherein the orbit angle $\phi$, between the projection of the central ray on the laminar plane and a straight line having a given angular position with respect to the line scanning direction of the television camera, is varied and a trapezium correction means for said apparatus; the improvement comprising means preceeding said trapezium correction means for electronically rotating the image field through said orbit angle $\phi$, and means following said trapezium correction means for restoring the position of said image field to its position before rotation thereof.

2. The apparatus of claim 1 wherein said superposition device comprises an image storage device.

3. The apparatus of claim 1 wherein said image field rotating means comprises means for superposing components of vertical frequency on horizontal deflection voltages or currents, and means for superposing components of horizontal frequency on vertical deflection voltages or currents.

4. The apparatus of claim 1 further comprising means for correcting for distortion caused by the structure of said image intensifier connected in series between said image field rotating means and said image field restoring means.

5. The apparatus of claim 4 wherein means are provided for applying the output of said restoring means to said television camera.

6. The apparatus of claim 1 wherein said superposition device comprises an image storage device, the output of said image field storing means being coupled to said image storage device.

7. The apparatus of claim 6 further comprising deflection means coupled to said television camera for correcting for distortions caused by the structure of said image intensifier.

* * * * *